US010265708B2

(12) United States Patent
Rhea et al.

(10) Patent No.: US 10,265,708 B2
(45) Date of Patent: Apr. 23, 2019

(54) PRESSURIZABLE FLUID CONTAINER AND FLEXIBLE DISPENSER

(71) Applicant: Lunatec, Inc., San Diego, CA (US)

(72) Inventors: Nick Rhea, San Diego, CA (US); Eric Young, La Mesa, CA (US)

(73) Assignee: Lunatec, Inc., San Diego, CA (US)

( * ) Notice: Subject to any disclaimer, the term of this patent is extended or adjusted under 35 U.S.C. 154(b) by 0 days.

(21) Appl. No.: 15/226,602

(22) Filed: Aug. 2, 2016

(65) Prior Publication Data

US 2016/0339454 A1 Nov. 24, 2016

Related U.S. Application Data

(63) Continuation-in-part of application No. 14/332,304, filed on Jul. 15, 2014, now Pat. No. 9,744,545.

(Continued)

(51) Int. Cl.
| | |
|---|---|
| *B05B 1/12* | (2006.01) |
| *B05B 1/30* | (2006.01) |
| *B05B 9/08* | (2006.01) |
| *F16K 7/06* | (2006.01) |
| *A61M 39/28* | (2006.01) |
| *B05B 11/00* | (2006.01) |
| *B05B 7/24* | (2006.01) |
| *B05B 15/30* | (2018.01) |
| *B05B 15/40* | (2018.01) |

(52) U.S. Cl.
CPC .............. *B05B 1/12* (2013.01); *A61M 39/286* (2013.01); *A61M 39/287* (2013.01); *B05B 1/30* (2013.01); *B05B 7/2418* (2013.01); *B05B 7/2424* (2013.01); *B05B 9/0816* (2013.01); *B05B 9/0822* (2013.01); *B05B 11/0094* (2013.01); *F16K 7/065* (2013.01); *F16K 7/066* (2013.01); *B05B 15/30* (2018.02); *B05B 15/40* (2018.02)

(58) Field of Classification Search
CPC B05B 1/12; B05B 1/30; B05B 7/2418; B05B 7/2424; B05B 9/0816; B05B 9/0822; B05B 11/0094; A61M 39/286; A61M 39/287; F16K 7/065; F16K 7/066
See application file for complete search history.

(56) References Cited

U.S. PATENT DOCUMENTS 1,439,295 A * 12/1922 Craig ........................ B67D 7/72
141/26
1,959,074 A * 5/1934 Bloxsom ............. A61M 39/286
251/6

(Continued)

*Primary Examiner* — Nicholas J. Weiss
(74) *Attorney, Agent, or Firm* — Hybrid Law Group P.C.

(57) ABSTRACT

A flexible dispensing apparatus for coupling to pressurized fluid containers is described. It includes a flexible tube and a handle assembly. The handle assembly houses a second end of the tube. The handle assembly has a first side connected to a second side, a slide trigger, a roller coupled to the bottom of the slide trigger with a dowel pin, a spray nozzle assembly, a magnet reservoir, and a magnet. The first side has an inclined ramp that runs along a length of the first side and extends into the second side above and beyond a seam that is formed by the connection of the two sides. The tube is within a channel in the handle assembly formed between the inclined ramp and the roller. When the roller is rolled toward the end of the ramp it pinches the flexible tube near the top of the inclined ramp.

4 Claims, 15 Drawing Sheets

Related U.S. Application Data

(60) Provisional application No. 62/200,996, filed on Aug. 4, 2015.

(56) References Cited

U.S. PATENT DOCUMENTS

| | | | | |
|---|---|---|---|---|
| 2,481,719 A * | 9/1949 | Buck | B05B 9/0816 | 222/108 |
| 2,595,511 A * | 5/1952 | Butler | A61M 39/286 | 251/6 |
| 2,706,586 A * | 4/1955 | Sikorski | G01F 11/028 | 222/400.8 |
| 3,135,259 A * | 6/1964 | Evans | A61M 39/286 | 137/561 R |
| 3,189,038 A * | 6/1965 | Von Pechmann | A61M 39/286 | 137/315.07 |
| 3,207,387 A * | 9/1965 | Brickman | B05B 9/0822 | 222/400.8 |
| 3,685,739 A * | 8/1972 | Vanier | B05B 1/12 | 239/333 |
| 3,685,787 A * | 8/1972 | Adelberg | A61M 39/286 | 251/6 |
| 3,701,478 A * | 10/1972 | Tetsuya Tada | B05B 1/14 | 239/333 |
| 3,893,468 A * | 7/1975 | McPhee | A61M 39/286 | 137/1 |
| 3,961,756 A * | 6/1976 | Martini | B05B 1/12 | 239/337 |
| 4,047,694 A * | 9/1977 | Adelberg | A61M 39/286 | 251/6 |
| 4,109,869 A * | 8/1978 | Brockelsby | B05B 1/12 | 239/333 |
| 4,238,108 A * | 12/1980 | Muetterties | A61M 39/286 | 251/6 |
| 4,270,725 A * | 6/1981 | Scott | A61M 39/286 | 251/6 |
| 4,337,791 A * | 7/1982 | Tech | A61M 39/286 | 137/556 |
| 4,406,440 A * | 9/1983 | Kulle | A61M 39/286 | 251/6 |
| 4,537,334 A * | 8/1985 | Spengler | A47L 11/1625 | 222/401 |
| 4,606,477 A * | 8/1986 | Spengler | A47L 11/1625 | 222/153.09 |
| 4,787,560 A * | 11/1988 | DeYoreo | A01G 25/145 | 222/174 |
| 5,190,079 A * | 3/1993 | Nakada | A61M 39/286 | 138/45 |
| 5,421,519 A * | 6/1995 | Woods | B05B 1/1654 | 222/402.17 |
| 5,568,912 A * | 10/1996 | Minami | A61M 5/14228 | 137/553 |
| 5,664,732 A * | 9/1997 | Smolen, Jr. | B05B 1/042 | 239/121 |
| 5,924,633 A * | 7/1999 | Brass | B05B 9/0816 | 239/373 |
| 6,138,875 A * | 10/2000 | Condon | B05B 7/0025 | 222/401 |
| 6,695,228 B2 * | 2/2004 | Odessa | B05B 9/0816 | 239/302 |
| 6,752,331 B2 * | 6/2004 | Wu | B05B 9/0822 | 239/373 |
| 7,131,558 B2 * | 11/2006 | de la Guardia | B05B 9/0822 | 222/209 |
| 7,178,699 B2 * | 2/2007 | Spray | B67D 1/1405 | 222/212 |
| 7,246,755 B2 * | 7/2007 | Hornsby | B05B 1/3436 | 222/153.13 |
| 7,571,889 B2 * | 8/2009 | Miyahara | A61M 39/287 | 251/4 |
| 8,313,081 B2 * | 11/2012 | Adelberg | F16K 7/066 | 251/6 |
| 8,777,131 B2 * | 7/2014 | Hudson | B05B 1/304 | 239/525 |
| 9,623,230 B2 * | 4/2017 | Kim | A61M 39/28 | |
| 9,839,927 B2 * | 12/2017 | Spang | B05B 1/12 | |
| 2007/0113893 A1 * | 5/2007 | Sun | F04B 33/00 | 222/209 |
| 2012/0091228 A1 * | 4/2012 | Tseng | B05B 7/0037 | 239/311 |
| 2012/0119121 A1 * | 5/2012 | Hopf | A61M 39/285 | 251/4 |

* cited by examiner

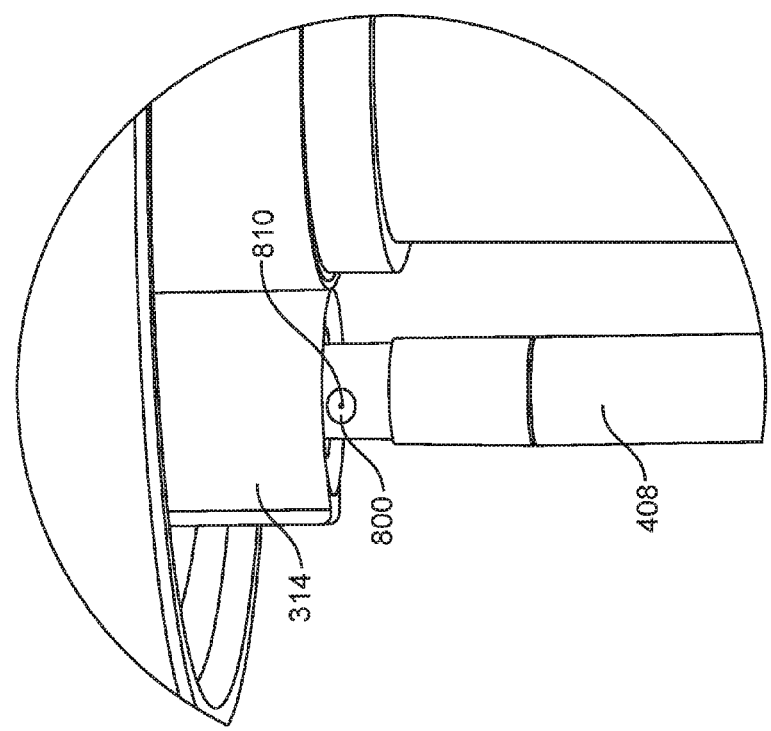
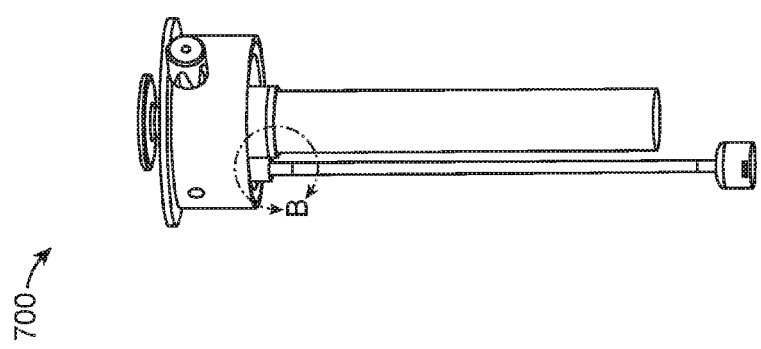
FIG. 8B
FIG. 8A

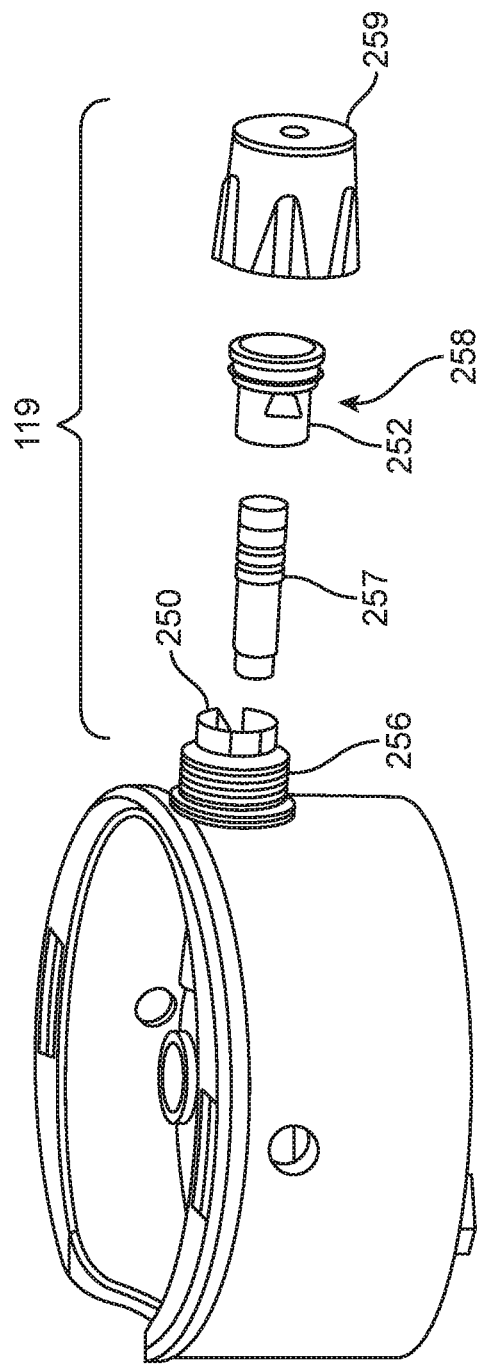

PRESSURIZABLE FLUID CONTAINER AND FLEXIBLE DISPENSER

This claims priority from U.S. Provisional Application Ser. No. 62/200,996, filed on Aug. 4, 2015, and is a continuation-in-part of and further claims priority from U.S. application Ser. No. 14/332,304, filed Jul. 15, 2014, both of which are incorporated herein by reference in their entireties.

FIELD OF THE INVENTION

The present invention relates generally to the field of outdoor recreational hydration equipment and fluid containers, in which the bottle or container must be squeezed or tilted to release the flow of fluid to allow for ease of drinking, washing, and/or cleaning and is particularly applicable to sports bottles, and the like. It also relates to hydration systems using a reservoir, such as fluid or water packs, water bladders and the like, in which a hose is used to suck the water from the bladder, pack or reservoir.

BACKGROUND OF THE INVENTION

In recent years, the number of health-conscious individuals has grown tremendously. In addition, research into the importance of clean water for hydration and other uses during health-improving activities: walking, hiking, biking, camping, and other outdoor activities has led to an increased need for fluid delivery devices that can provide fluids through a secure and hygienic means. Conventional fluid delivery devices, such as water bottles, are useful for various purposes in activities such as athletic, outdoor, recreational, or other uses. Typically, such devices are designed for a user to carry water, electrolytic fluid replacement drinks, or any type of liquid or, in some cases, powders or other materials. In many cases, these devices are used to enable active people: walkers, hikers, riders, and campers to drink or replenish fluid loss without stopping their particular activity. Additionally such devices may be used by these individuals as a source of water to clean themselves, their utensils and tools.

Depending on the type of fluid dispensing system, constant or frequent use of fluid containing devices and bottles can lead to damage to, for example, the pull-valve, or loss of a screw-type cap or pop-on/pop-off lid. Furthermore, for squeeze-type containers, the frequent deformation of the container can lead to structural failure of the walls of the container. Additionally, the ability to control water flow to clean or wash can be difficult as the fluid dispensing device must be tilted at a particular angle and/or squeezed to initiate the flow of water.

Additionally, transmission of germs and the inclusion of foreign material into the fluid becomes an increased risk from the constant and repetitive touching of the mouth to the pull-valve or rim and/or the repetitive opening of the container, exposing the contents to the environment.

Furthermore, the mechanical stress of repetitive opening and, in some cases, squeezing the bottle, may result in damaged or lost parts and a shortened product life span.

As a result of the above-stated problems and desires, there is a need for a fluid container, without the limitations of conventional fluid containers.

In addition, typical hydration systems using a reservoir, hose and bite valve, such as pouch bladders with a hose and bite valve that slide into a backpack or sack, are prone to puncturing, tearing, leaking, and suffer from poor drying of the reservoir after use. In addition, to start the flow of water, one must be able to create a sufficient suction to start the flow of water, which may be especially difficult in an exhausted state. Because of the bladders malleable nature, filling such devices is typically difficult to do without spilling fluid. These devices are also not practical if there is no backpack to put them in, and thus lose a lot of their use unless there is a pack to stow them within. These types of hydration systems also lack pressure to spray the contents on surfaces, rendering their use strictly for hydration. Furthermore, traditional bladders and hose hydration systems are difficult to directly attach water purification devices to. Finally, none of these systems have the capability of providing variable spray patterns at the users discretion. So while they may be used to provide water or fluid for drinking, they are incapable of providing mist to cool off or a powerful shower spray or single powerful stream to wash oneself or to wash other equipment.

Thus, what is needed are water or fluid bottles that are convenient to handle, easily pressurized to provide a strong powerful spray, and that have adjustable nozzles for different uses. What is further needed are flexible hoses and handles for such hoses that can be used with pressurized bottles and that themselves also have adjustable nozzles for different uses and capable of delivering strong powerful and adjustable release of fluids, such as water.

SUMMARY OF THE INVENTION

In one aspect of the invention, a flexible dispensing apparatus for coupling to pressurized fluid containers is described. The said flexible dispensing apparatus includes a flexible tube and a handle assembly. The flexible tube has a first end and a second end. The first end can have a nozzle connector for connecting the flexible tube to a pressurized fluid container. The handle assembly houses the second end of the flexible tube. The handle assembly has a first side connected to a second side, a slide trigger, a roller coupled to the bottom of the slide trigger with a dowel pin, spray nozzle assembly, a magnet reservoir, and a magnet. The first side of the handle assembly has an integrated inclined ramp that runs along a length of the first side and extends into the second side above and beyond a seam that is formed by the connection of the two sides. The flexible tube is housed within a channel in the handle assembly formed between the inclined ramp and the roller, such that when the roller is rolled toward the end of the ramp with the slide trigger it pinches the flexible tube near the top of the inclined ramp thereby prohibiting the flow of fluid to the spray nozzle assembly.

In another aspect of the invention, a fluid containment and delivery system is described. The system includes a pressurized fluid container having a cap with a threaded cap nozzle and a flexible dispensing apparatus. The flexible dispensing apparatus has a flexible tube and a handle assembly. The flexible tube has a first end and a second end. The first end has a threaded nozzle connector for connecting the flexible tube to the threaded cap nozzle of the pressurized fluid container. The handle assembly houses the second end of the flexible tube. The handle assembly has a first side connected to a second side, a slide trigger, a roller coupled to the bottom of the slide trigger with a dowel pin, a spray nozzle assembly, a magnet reservoir, and a magnet. The first side of the handle assembly has an integrated inclined ramp that runs along a length of the first side and extends into the second side above and beyond a seam that is formed by the connection of the two sides. The flexible tube is housed within a channel in the handle assembly formed between the inclined ramp and the roller, such that when the roller is rolled toward the end of the ramp with the slide trigger it pinches the flexible tube near the top of the inclined ramp thereby prohibiting the flow of fluid to the spray nozzle assembly.

In yet another aspect of the invention, a tripe type variable spray nozzle is described. It has a first threaded nozzle formed integrally with a cap of a pressurized fluid container or a handle assembly of a flexible dispensing apparatus. It also has a barbed fitting with a proximal end that is nested within the first threaded nozzle. Additionally, it has a shower type outlet nozzle with three or more shower holes. The shower type outlet nozzle is coupled to a distal end of the barbed fitting. An outlet cap having a single fluid outlet hole is fitted over the shower type outlet nozzle. The outlet cap has a threaded portion that mates with the first threaded nozzle by screwing the outlet cap onto the first threaded nozzle. The triple type variable spray nozzle is capable of releasing pressurized fluid as a stream or as a mist by adjusting how tightly the outlet cap is screwed onto the first threaded nozzle, or as a shower spray by completely removing the outlet cap.

Other objects and advantages of the present invention will become apparent from the following descriptions, taken in connection with the accompanying drawings, wherein, by way of illustration and example, various embodiments of the present invention are disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

FIG. 8a is another perspective view of the pressurizing cap assembly shown in FIG. 4.

FIG. 8b is a close-up perspective view of Section B shown in FIG. 8a.

FIG. 9 is a exploded view of a nozzle of a pressurizing cap assembly in accordance with another embodiment

FIG. 14b is a perspective view of the underside of the trigger lock shown in FIG. 15a.

FIG. 15b is a side cut-out view of the trigger lock and cap shown in FIG. 16a.

DETAILED DESCRIPTION OF THE PREFERRED EMBODIMENT

Various embodiments or examples may be implemented in numerous ways, including as a system, a process, or an apparatus. A detailed description of one or more examples is provided below along with the accompanying figures. The detailed description is provided in connection with such examples, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For clarity, technical material that is known in the technical fields related to the examples has not been described in detail to avoid unnecessarily obscuring the description. Components, elements or parts shown in some figures may be combined with components, elements or parts shown in other figures, and various aspects of each embodiment may be combined or incorporated into other embodiments.

Figure 1:
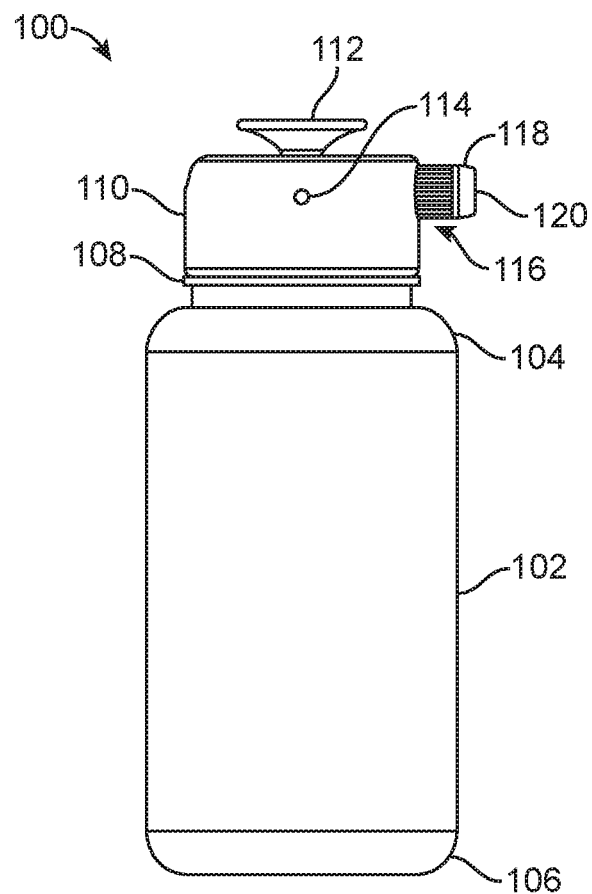
FIG. 1 is a side view of one embodiment of a pressurized fluid container in accordance with the present invention.

Referring now to FIG. 1, bottle assembly 100 includes body 102, it may include a top radius 104, a bottom radius 106, a thread lip 108, a cap body ("cap") 110, a pressurizing plunger ("plunger") 112, a teeter valve pivot 114, a nozzle base 116, an adjustable spray screw cap 118, and spray nozzle 120.

In one or more embodiments, body 102 may have a threaded portion (not pictured here) upon which the cap 110 (sometimes referred to as a lid) may be screwed onto. Plunger 112 is disposed through the cap 110 and is used to pressurize the body 102. Adjustable spray screw cap 118 is threaded onto nozzle base 116. By turning the adjustable spray screw cap 118, the position of spray nozzle 120 is modified within nozzle base 116 thus changing the characteristics of the spray. For example, the tighter the spray screw cap 118 is screwed onto the nozzle base 116 the finer the mist that is released through the opening in the spray screw cap 118. As the spray screw cap 118 is loosened (turned in the opposite direction), the mist turns into a stream rather than a mist.

In one embodiment, as shown in FIG. 9, the nozzle 119 forms a triple type variable spray nozzle. It is made up of a first threaded nozzle 256 formed integrally with cap 110, a barbed fitting 257 with a proximal end that is nested within the first threaded nozzle 256, shower type outlet nozzle 258 with three or more shower holes, shower type outlet nozzle 258 being coupled to a distal end of the barbed fitting 257, and spray screw cap 259 (also referred to as an outlet cap). Spray screw cap 259 may have just one hole as shown in FIG. 9. The spray screw cap (or outlet cap) 259 is fitted over the shower type outlet nozzle 258, the outlet cap 259 having a threaded portion that mates with the first threaded nozzle 256 by screwing the outlet cap 259 onto the first threaded nozzle 256. The triple type variable spray nozzle 119 is capable of releasing pressurized fluid as a stream or as a mist by adjusting how tightly the outlet cap 259 is screwed onto the first threaded nozzle 256. To achieve a shower spray effect, the outlet cap 259 is completely removed by unscrewing it from the first threaded nozzle 256 completely. As a result, the cap 110 is uniquely capable of turning a normal water bottle into a water bottle that is capable of spraying a mist, a stream or a powerful shower spray with a single press rather than repeated squeezing as will be described further below.

Figure 2:
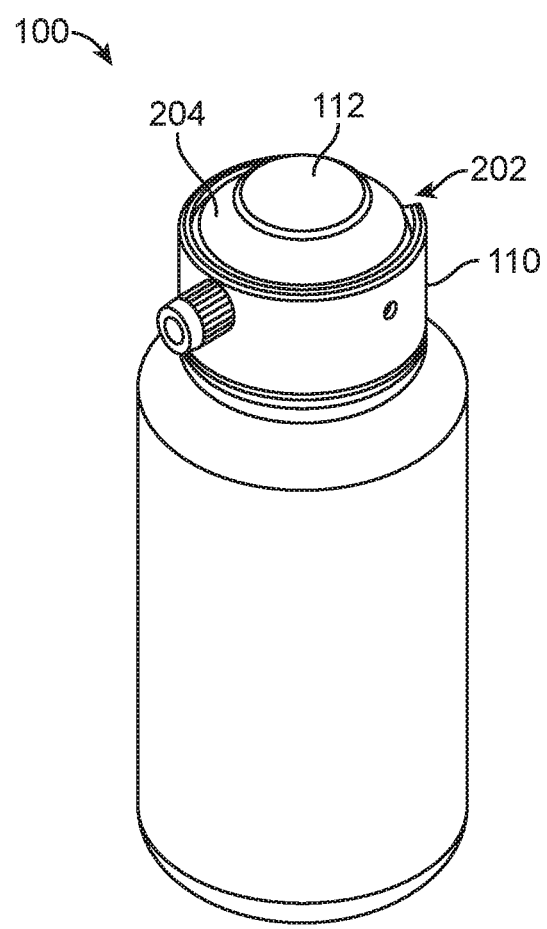
FIG. 2 is a perspective view of the top front of the pressurized fluid container shown in FIG. 1.

Returning now to FIGS. 2 and 3, the spray is activated by depressing a teeter valve (not pictured here) which pivots on an axis transverse through the diameter of the cap 110 located at the teeter valve pivot 114. FIG. 2 depicts the assembled bottle assembly 100 and further depicts a cut-away portion 202 of the cap 110. The teeter valve 204 is shown located between the cap 110 and the plunger 112. The teeter valve 204 forms a disc that fits just within the diameter of the cap 110. The disked teeter valve 204 pivots at substantially about its diameter.

Figure 3:
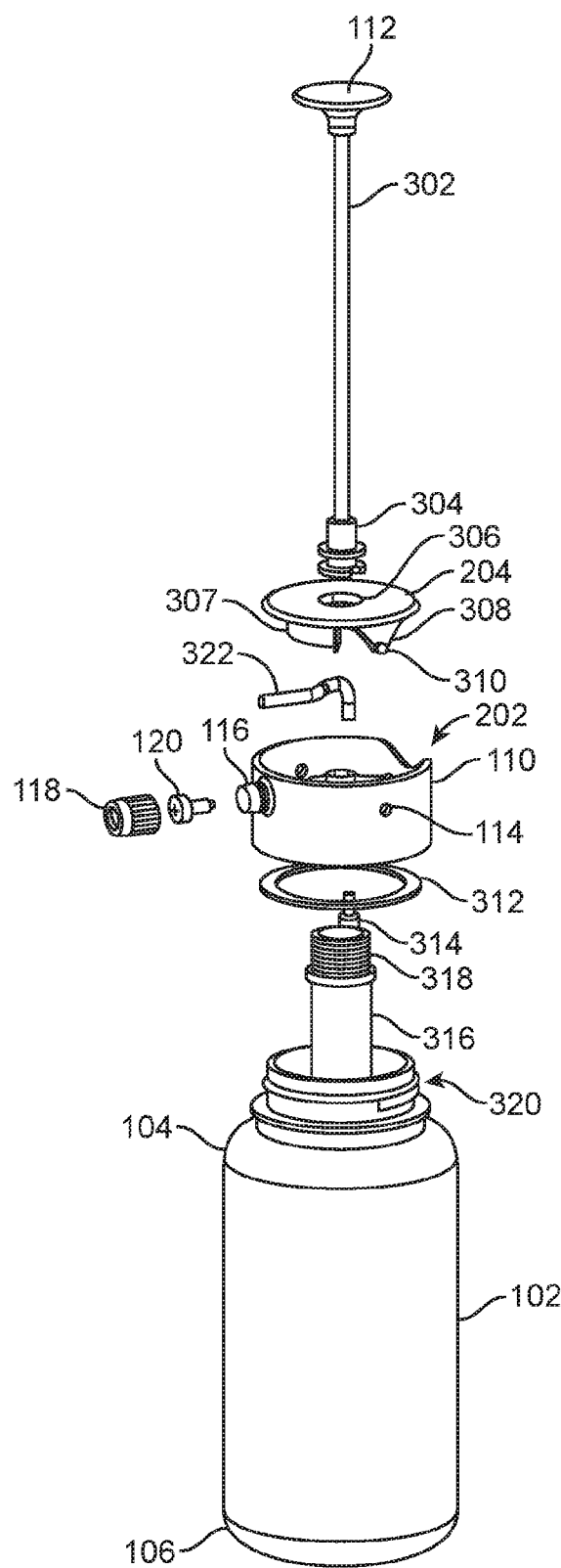
FIG. 3 is an exploded perspective view of the pressurized fluid container shown in FIG. 1.

Referring now to FIG. 3 which shows a exploded perspective view of the left side of the bottle assembly 100. Plunger shaft 302 has a top end which is connected to the plunger 112 and a bottom end which is connected to the stopper 304. The stopper 304 may contain at least one of a multiple of flanges to produce pressure within the bottle/container cavity or body 102.

The plunger shaft 302 is disposed through an opening 306 in the teeter valve 204, and opening 306 is preferably in the center of the teeter valve 204. The teeter valve 204 pivots on an axis through the cap 110 and that axis is aligned with the teeter valve pivots 114, which are on opposite sides of the teeter valve 204. Opening 306 is aligned with the pivot axis, i.e., it is aligned with the teeter valve pivots 114. This pivot is accomplished by a pair of teeter valve flanges 308 projecting down on the underside of the teeter valve 204 and on opposite sides of the teeter valve 204. Pivot tabs 310 are located at the lower tips of the teeter valve flanges 308. These pivot tabs 310 extend partially into the teeter valve pivots 114 in the cap 110.

Figure 4:
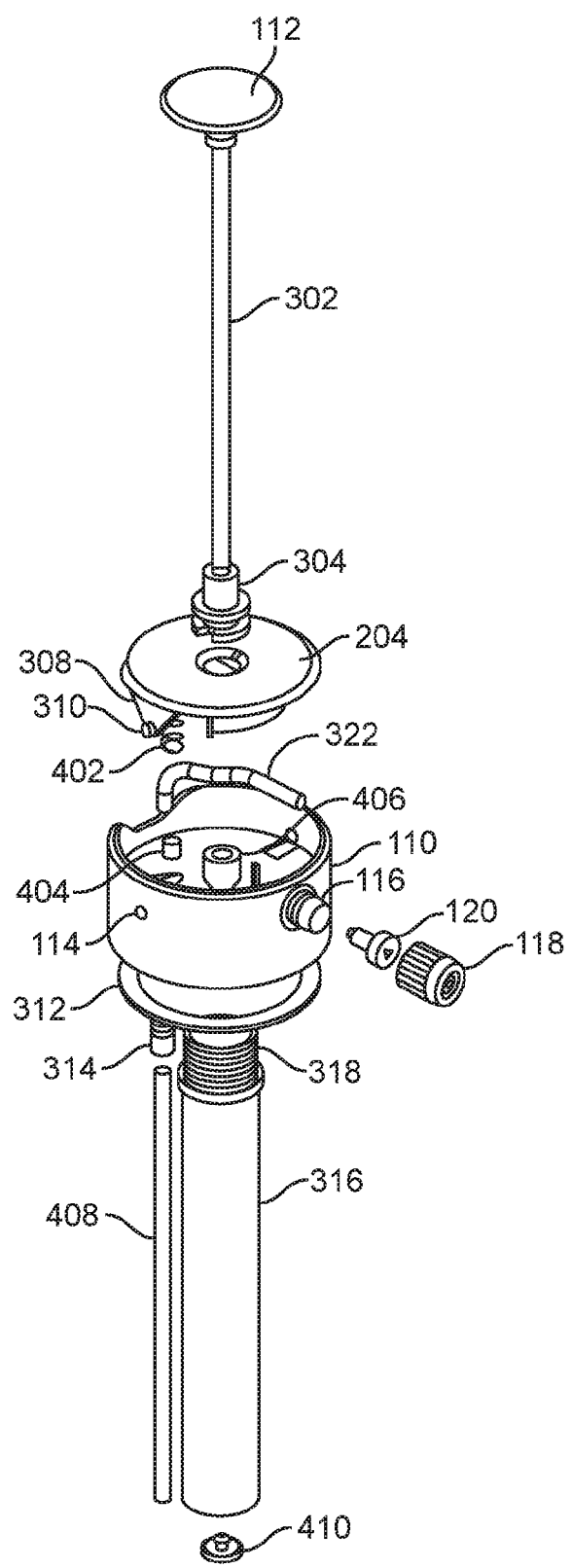
FIG. 4 is an exploded perspective view of the right side a pressurizing cap assembly in accordance with one embodiment of the invention.

Referring now to FIG. 4, a return spring 402, is disposed between the teeter valve 204 and the cap 110. Return spring 402 is located on extrusion 404, on the interior top surface of cap 110. The return spring 402 is behind opening 306 and plunger shaft 302 and pushes up against the bottom of the back end of teeter valve 204. This causes the front end of teeter valve 204 to pivot downward causing valve lock lip 307 (extending down from the bottom of the front side of teeter valve 204) to push down against and pinch flexible conduit 322. Valve lock lip 307 is arcuate and tracks the circumference of teeter valve 204. Thus, in its resting state, teeter valve 204 prohibits fluid or water from flowing through flexible conduit 322 past the pinch point where valve lock lip 307 presses down against flexible conduit 322. When the back end of teeter valve 204 is pressed to activate a spray discharge, return spring 402 is compressed and teeter valve 204 pivots on pivot tabs 310, raising the front end of teeter valve 204. This raises valve lock lip 307 off of flexible conduit 322, releasing the pressure off of flexible conduit 322 and allowing for pressurized fluid or water to flow past the pinch point and out nozzle 120 of cap 110.

In one embodiment, cap 110 is removably connected to body 102 by a threaded portion 320 of body 102 and a mirror threaded portion (not pictured here) on the interior of cap 110. To further seal this connection, a washer 312 is disposed between the body 102 and the cap 110.

The stopper 304 is disposed within the pump shaft 316. The pump shaft 316 has two ends, an upper end which has a threaded portion 318 and a lower end (not pictured here). The threaded portion 318 of the pump shaft 316 is rotatably attached to the underside of the cap 110.

A relief tube 314 has both a first ("upper") end and a second ("lower") end. Relief tube 314 allows the pressurized fluid to escape the body 102. In one embodiment, the upper end of relief tube 314 may be press-fit into the underside of the cap 110 utilizing an o-ring (not pictured) to form a seal.

A flexible conduit 322 has both a first ("upper") end and a second ("lower") end. The lower end of flexible conduit 322 is connected to the relief tube 314. Pressurized fluid which rises through the relief tube 314, passes through the cap 110 and then, in one or more embodiments, the upper end of relief tube 314 may be barbed to connect to the flexible conduit 322. The upper end of the flexible conduit 322 passes through nozzle base 116 and is attached to the spray nozzle 120. In one or more embodiments, the spray nozzle 120 may be barbed, and flexible conduit 322 is press-fit over the barbs to form a connection. The pressurized fluid, having entered the nozzle base 116, then attains the desired spray characteristics determined by the positioning of the adjustable spray screw cap 118 and the spray nozzle 120 as described in more detail above.

The plunger shaft 302 is disposed within a shaft guide 406. When depressed, air is forced into the pump shaft 316 and into body 102 through a one-way pump valve 410 that allows air to flow past the valve into body 302 but not backwards into pump shaft 316. This causes pressure to increase within body 102. A relief tube extension 408 is connected to relief tube 314, which in turn is connected to the underside of cap 110. In one embodiment, relief tube extension 408 may be press-fit into relief tube 314. A through hole 606 (shown in FIG. 6) in cap 110 then connects the flexible conduit 322 to relief tube 314. This relief extension 408, relief tube 314 and flexible conduit 322 then conduct the pressurized fluid to nozzle base 116.

Figure 5:
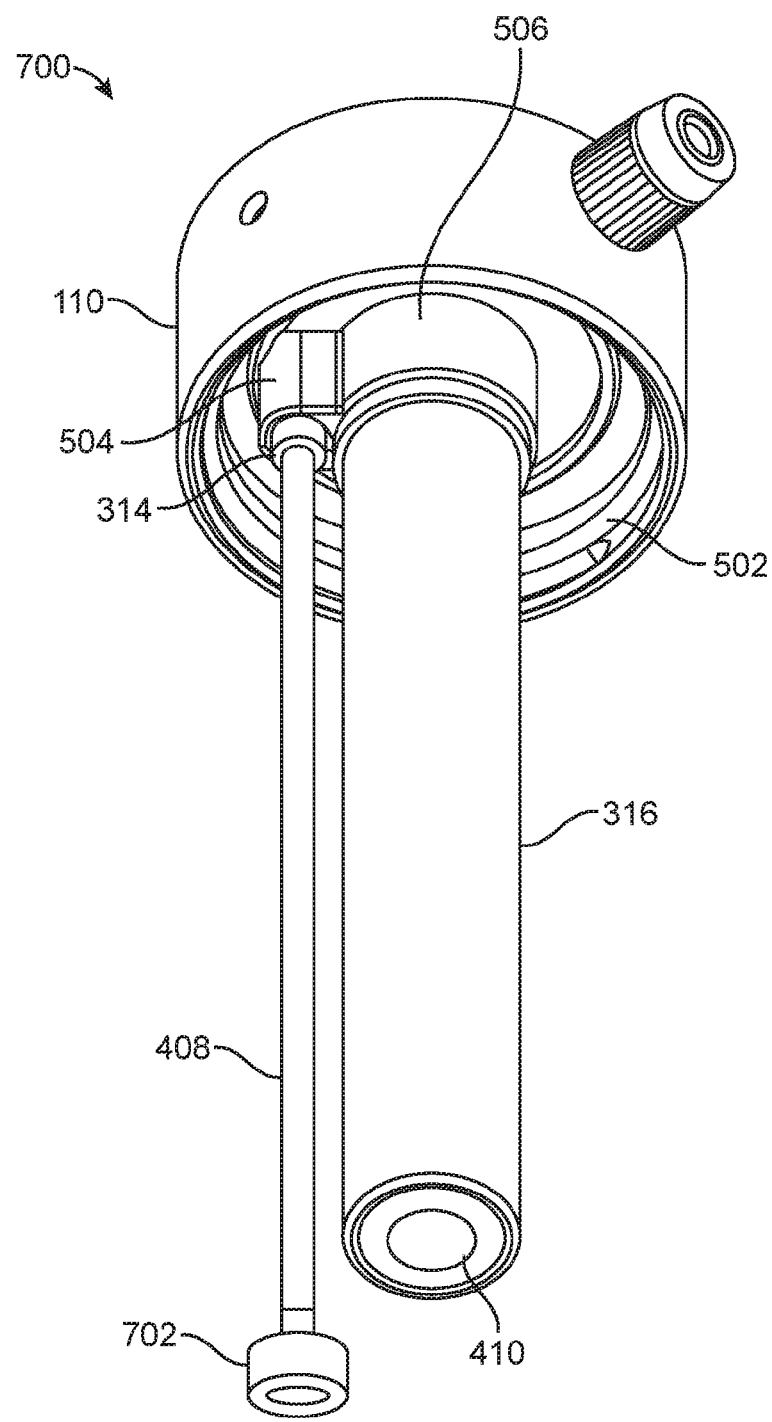
FIG. 5 is a perspective view of the underside of the pressurizing cap assembly shown in FIG. 4.

FIG. 5 depicts the underside of the assembled pump and valve mechanism of one or more of the preferred embodiments. Cap insert assembly 700 includes the interior threaded portion 502 of the underside of cap 110, which is used to connect to and disconnect from the body 102 (not pictured here). Housing 504 contains the through hole 606 (not pictured here) for the relief tube 314 and is disposed on the underside of the cap 110, as is the threaded connector 506 for pump shaft 316. Filter assembly 702 is removably attached to the relief tube extension 408. Filter assembly 702 serves two purposes. It prohibits particulates to travel up relief tube extension 408 and then out the nozzle, thus ensuring that water or fluids that the user drinks is clean. It also serves a completely different purpose. It can be weighted so that when the bottle is held upside down and is not full or is nearly empty, the filter falls down toward cap 110 and stays within the fluid. This is possible because relief tube extension 408 can be made of a flexible plastic tube that can easily bend and be fluid. Thus, filter assembly 702 acts as a fluid capture weight allowing the bottle to be used to spray fluid even when the bottle is upside down and isn't full of fluid or is nearly empty of fluid. Filter assembly 702 (or fluid capture weight) therefore allows the user to still obtain a stream of fluid even when the bottle is upside and nearly empty.

Figure 6:
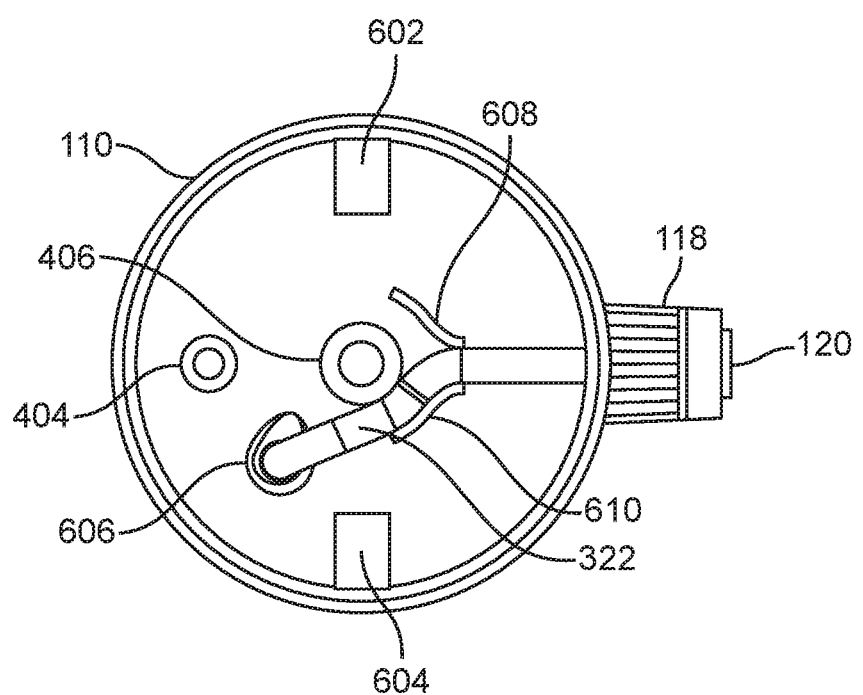
FIG. 6 is a top view of the interior of the pressurizing cap assembly of FIG. 4.

Referring now to FIG. 6, cap 110 is viewed from the top with teeter valve 204 and plunger 112 removed for clarity. Detents 602 and 604 allow clearance and free movement for pivot flanges 308 on interior surface of cap 110. Through hole 606 provides a connection point for the lower end of flexible conduit 322. Flexible conduit 322 is then routed across the upper interior surface of cap 110 by guides 608 and 610. The upper end of flexible conduit 322 is then connected to the barbed nozzle base 116 (not pictured here).

Figure 7:
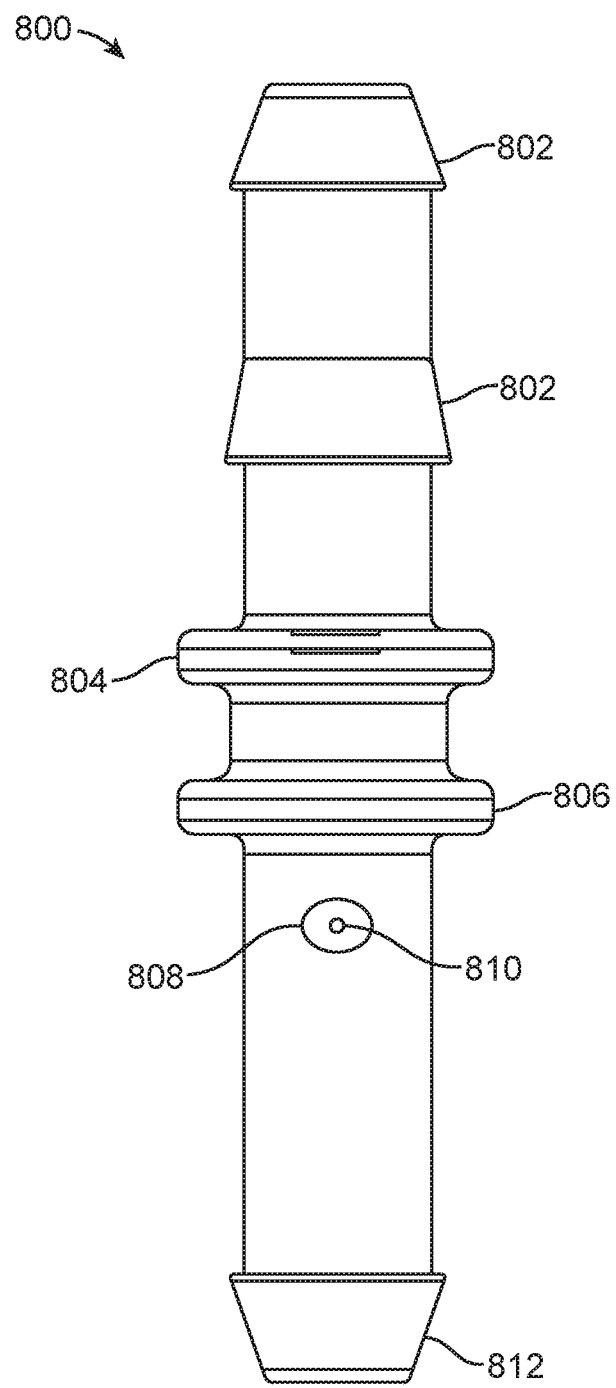
FIG. 7 is a side view of the uptake adapter assembly in accordance with one aspect of the invention.

Referring now to FIG. 7, uptake adapter assembly 800 has a first end and a second end. Upper flanges 802 are disposed at the first end of uptake adapter 800 and inserted into relief tube 314 (not pictured). A first hose seat 804 and a second hose seat 806 are positioned adjacent to each other. An intake indention 808 is positioned adjacent to the second hose seat 806. An intake hole 810 is centered within the intake indention 808. Lower flange 812 is disposed at the second end of the uptake adapter 800 and inserted into relief tube extension 408 (not pictured).

Referring now to FIG. 8a, cap insert assembly 700 is shown as an isometric view with a detailed inset, which is shown in close-up view in FIG. 8b. FIG. 8a illustrates the positioning of the uptake adapter assembly 800 between the relief tube 314 and the relief tube extension 408.

Intake indentation 808 and intake hole 810 serve the purpose of mixing air into the released fluid at the user's discretion. Allowing air to be mixed in with the fluid allows the user to conserve fluid while still providing a powerful stream, mist or shower to be released from nozzle 116. Thus, for example, if the user wants to use the fluid from the bottle to wash dishes while camping and wants to conserve water while enabling a powerful spray, he or she can pull relief tube extension 408 downward slightly to expose intake indentation 808 and intake hole 810, which allows air to be mixed in with the released fluid. Pushing relief tube extension 408 upward to cover intake indentation 808 and intake hole 810 prevents any air from mixing with the fluid or water.

Figure 10:
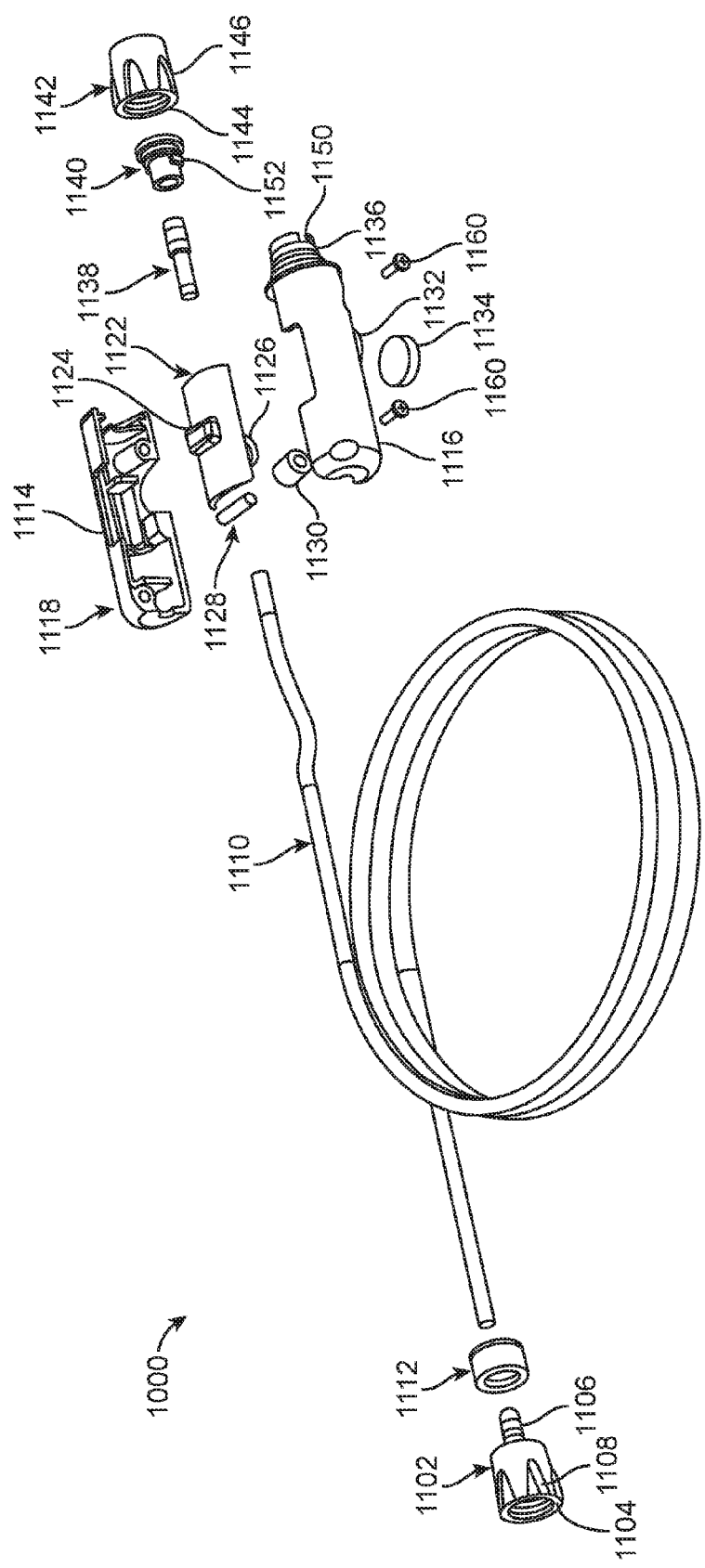
FIG. 10 is an exploded perspective of a flexible dispensing apparatus in accordance with one embodiment.

Turning now to FIG. 10, one embodiment of a flexible dispenser apparatus 1000 for a pressurized water container is shown. It includes a nozzle connector 1102 with a threaded connection 1104 to allow attachment to the outlet of a pressurized hydration device, such as that depicted in FIGS. 1-9, through, e.g., nozzle 116 of such a device. Nozzle connector 1102 has a second barbed press-fit portion 1106 at the other end for attaching to the first end of a flexible tube 1110. The nozzle connector 1102 may have knurled or grooved features 1108 to provide a better grip. A compression collar 1112 fits over the barbed press-fit portion 1106 of nozzle connector 1102 to secure flexible tube 1110. A second end of flexible tube 1110 runs through a handle assembly 1114 of the apparatus.

Handle assembly 1114 has a first side 1116 and a second side 1118. First side 1116 and second side 1118 may be connected to one another by screws 1160 (either two, three or four screws can be used, or possibly more). Handle assembly 1114 may enclose a slide trigger 1122. Slide trigger 1122 may have a raised portion 1124 to enable easy movement of slide trigger 1122 back and forth, i.e., longitudinally in the body of handle assembly 1114. Slide trigger 1122 also a holed flange 1126. Holed flange 1126 allows a roller 1130 to be affixed to slide trigger 1122 with a dowel pin 1128. The movement of slide trigger 1122 within handle assembly 1114 controls the flow of liquid through flexible tube 1110 by moving the roller 1130 back and forth on ramp 1120 which is inclined relative to the length of the handle assembly 1114 thereby compressing flexible tube 1110 between the roller 1130 and ramp 1120.

Flexible tube 1110 exits handle assembly 1114 and is affixed to a second barbed fitting 1138. Barbed fitting 1138 is fitted into an outlet nozzle 1140. Outlet nozzle 1140 and barbed fitting 1130 are held in position by an outlet cap 1142 which may have a threaded portion 1144. The threaded portion 1144 of outlet cap 1142 is threaded onto a corresponding threaded portion 1136 of handle assembly 1114. Outlet cap 142 may have knurled or grooved features 1146 to provide a better grip.

Figure 11:
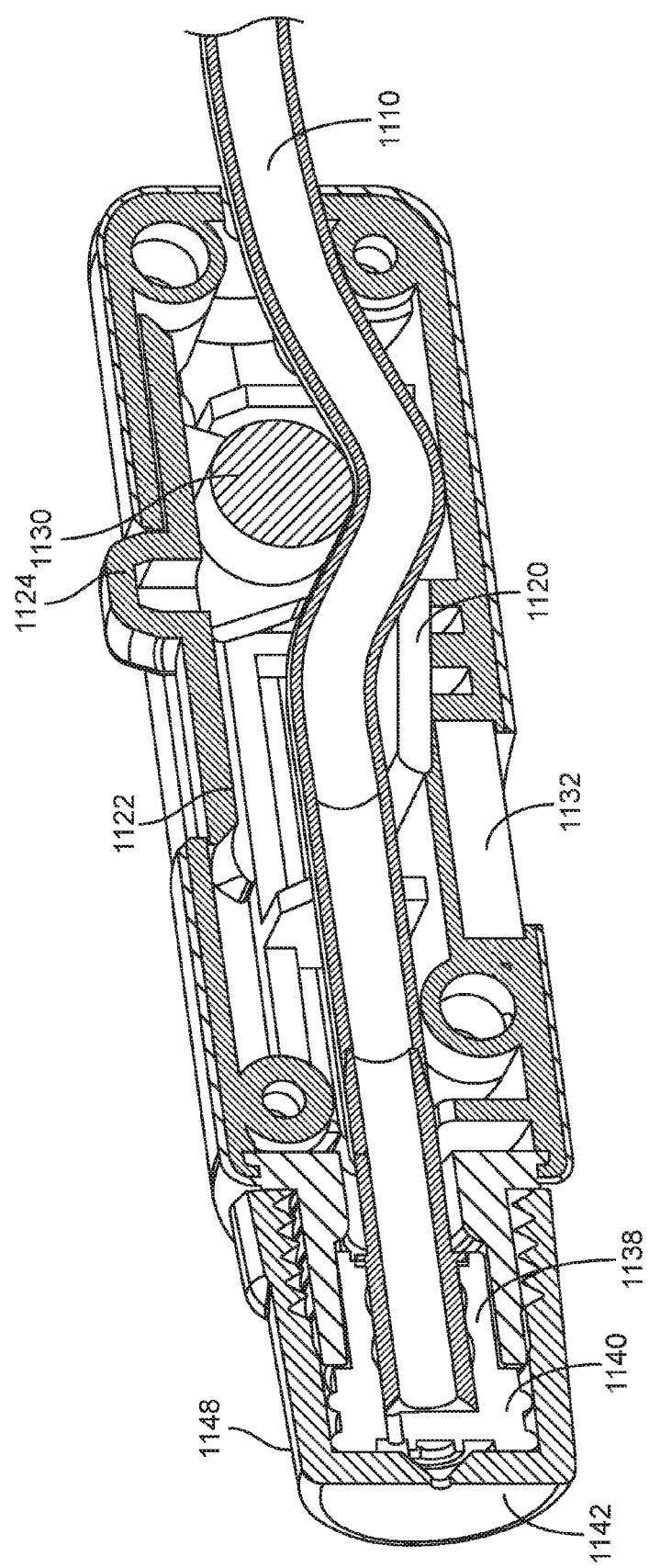
FIG. 11 is a cut-out side perspective view of the handle assembly of the fluid containment and delivery system shown in FIG. 10.

In one embodiment, as shown in FIGS. 10 and 11, first side 1116 contains a spray nozzle assembly 1148. The spray nozzle assembly 1148 can form a triple type variable spray nozzle that has a first threaded nozzle 1136 formed integrally with a distal end of the first side 1116 of the handle assembly 1114, a barbed fitting 1138 with a proximal end that is nested within the first threaded nozzle 1136, a shower type outlet nozzle 1140 with three or more shower holes, shower type outlet nozzle 1140 being coupled to a distal end of the barbed fitting, and an outlet cap 1142 having a single fluid outlet hole, wherein the outlet cap 1142 is fitted over the shower type outlet nozzle 1140. Outlet cap 1142 has a threaded portion 1144 that mates with the first threaded nozzle 1136 by screwing the outlet cap 1142 onto the first threaded nozzle 1136. The triple type variable spray nozzle is capable of releasing pressurized fluid as a stream or as a mist by adjusting how tightly the outlet cap 1142 is screwed onto the first threaded nozzle 1136. To achieve a shower spray effect, the outlet cap 1142 is removed by unscrewing it from first threaded nozzle 1136 completely. As a result, spray nozzle assembly 1148 is uniquely capable of spraying a mist, a stream or a powerful shower spray with a single press rather than repeated squeezing.

First side 1116 of handle assembly 1114 can further include a recessed portion 1132 or cavity configured to house a magnet 1134 that allows for attachment of the handle assembly 1114 to a ferrous surface.

As shown in FIG. 11 (applicable also to the nozzle assembly shown in FIG. 9) first threaded 1136 nozzle has a pair of opposing anti-rotation notches 1150 (anti-rotation notches 250 in FIG. 9) that mate with a pair of corresponding anti-rotation protuberances 1152 (anti-rotation protuberances 252 in FIG. 9) on the shower type outlet nozzle 1140 (shower type outlet nozzle 258 in FIG. 9), such that when outlet cap 1142 (outlet cap 259 in FIG. 9) is fitted over shower type outlet nozzle 1140 and screwed onto first threaded nozzle 1136, shower type outlet nozzle 1136 is prohibited from rotating with outlet cap 1142.

Figure 12:
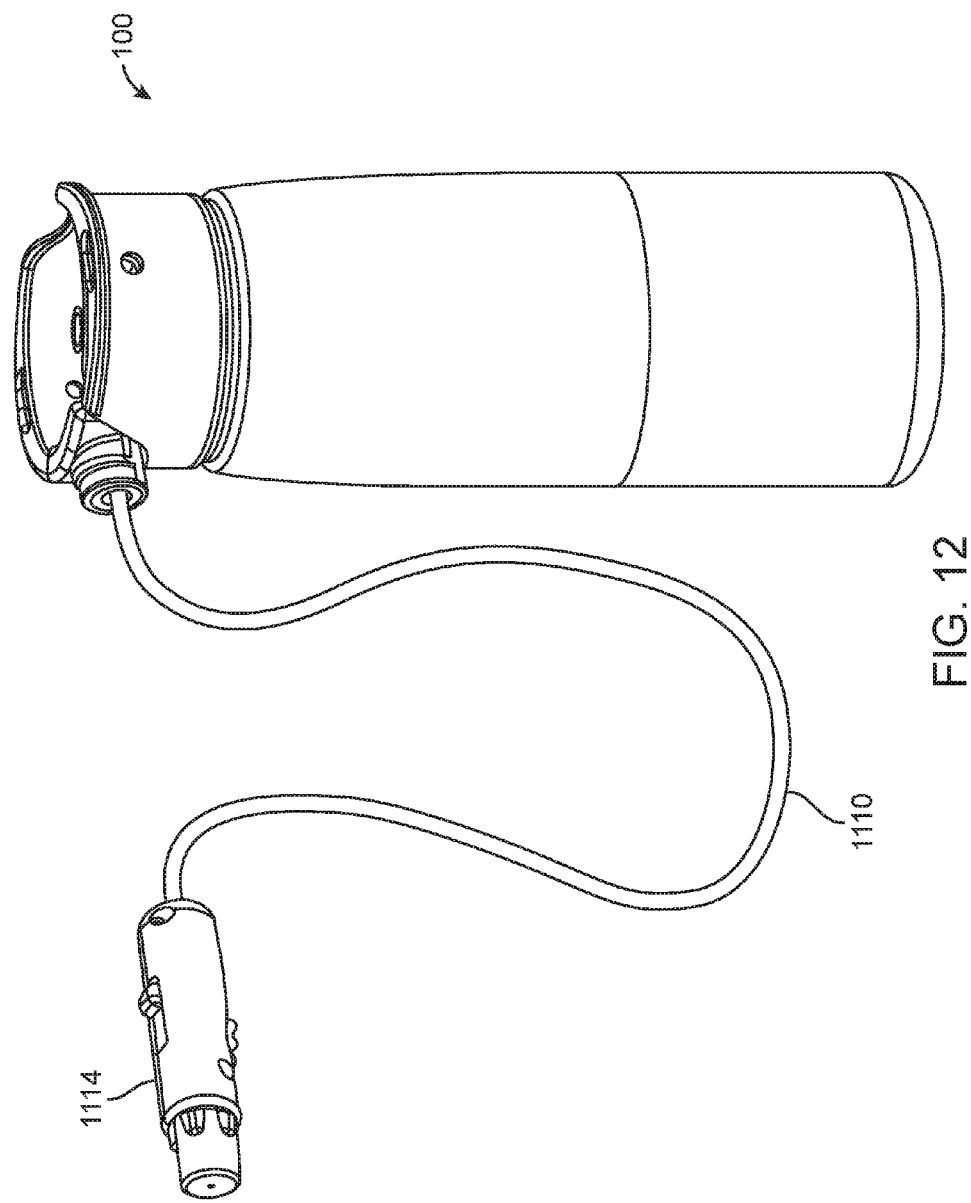
FIG. 12 is a side perspective view of fluid containment and delivery system in accordance with one embodiment.
Figure 13:
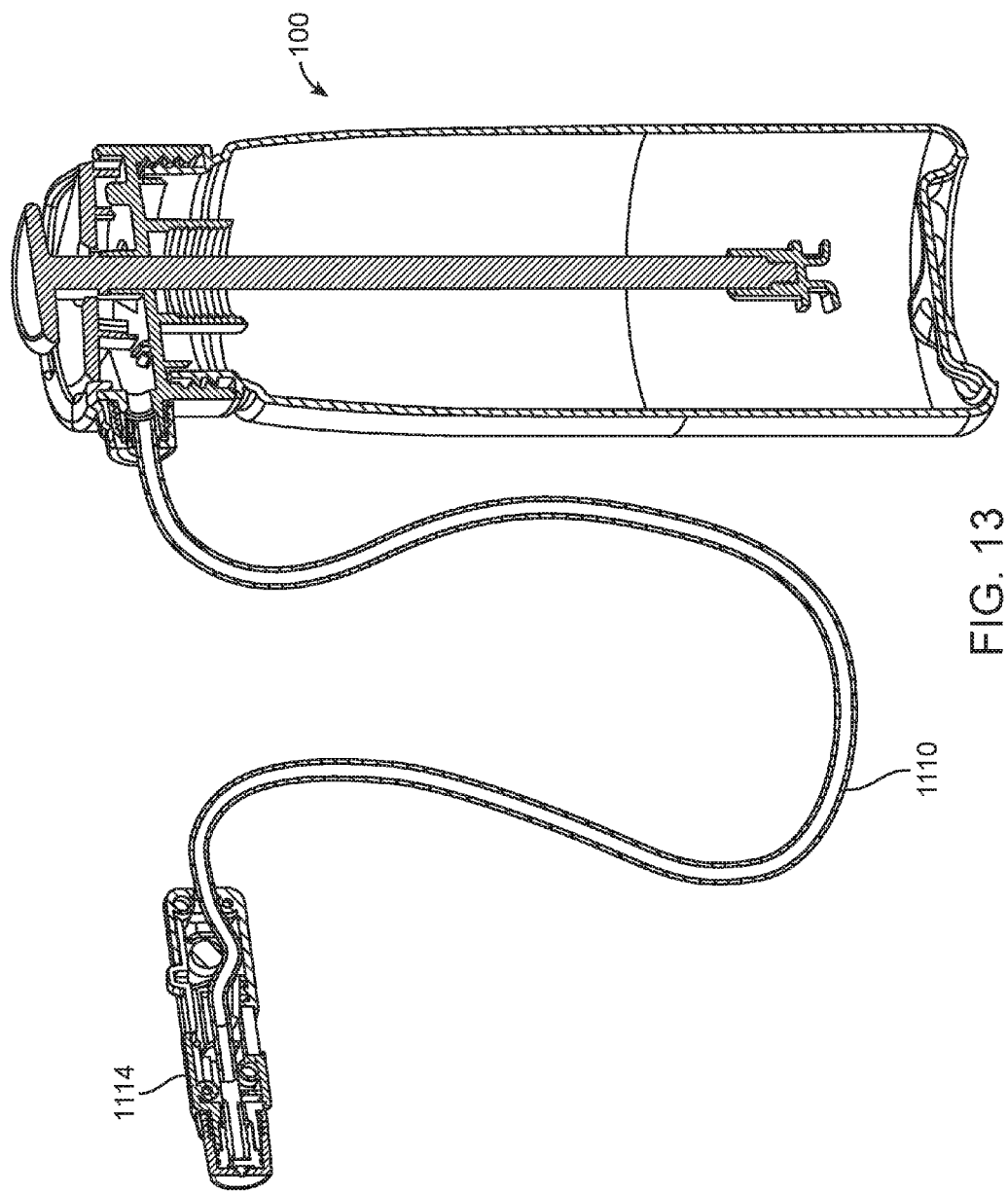
FIG. 13 is a cut-out side perspective view of the fluid containment and delivery system depicted in FIG. 11.

Turning now to FIGS. 12 and 13, a fluid containment and delivery system is depicted. The fluid containment and delivery system has a pressurized fluid container 100, such as the one described above with respect to FIGS. 1-9, and a flexible dispensing apparatus, such as the one described above with respect to FIGS. 10 and 11 having a handle assembly 1114 and a flexible tube 1110. The flexible dispensing apparatus can be connected to the pressurized fluid container 100 in the manner described above by forming a connection between the connector 1104 and the container's nozzle 116.

Figure 14A:
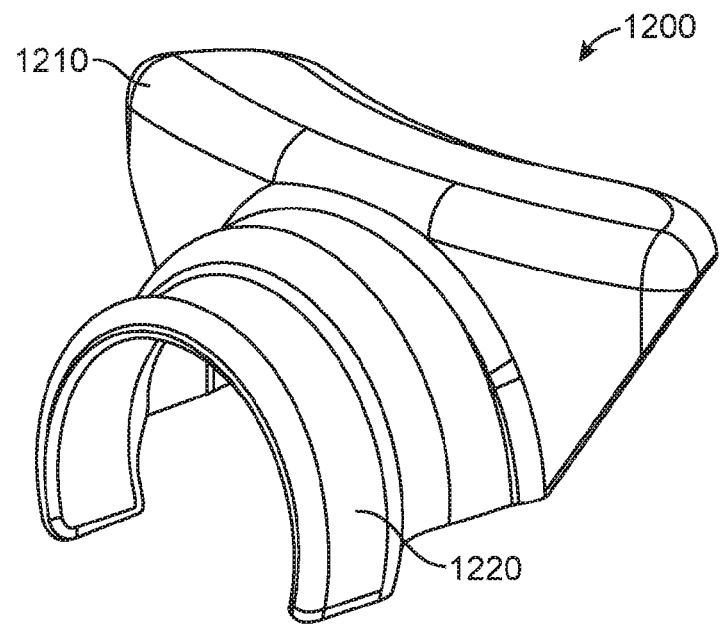
FIG. 14a is a perspective view of a trigger lock for a pressurized container in accordance with one aspect of the invention.
Figure 14B:
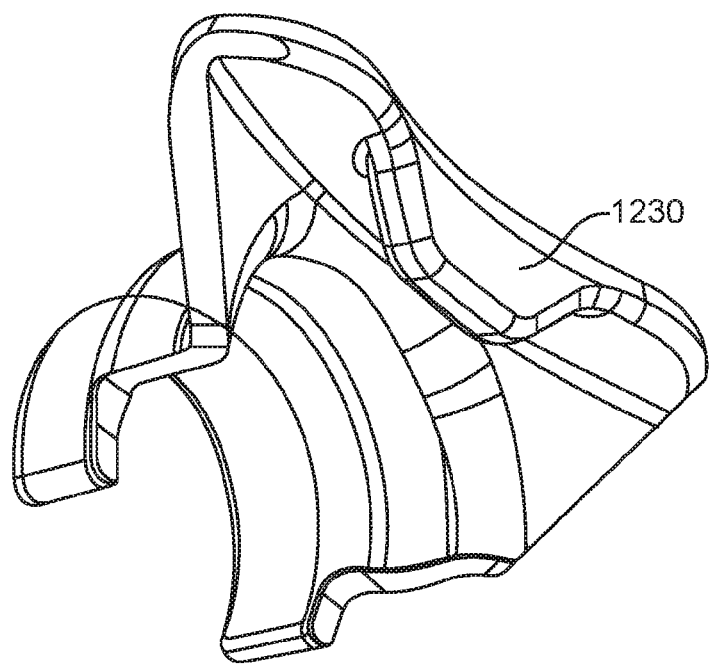

FIGS. 14a and 14b depict a trigger lock 1200 that can be used with the fluid containment and delivery system shown in FIGS. 12 and 13 to ensure constant flow of fluid to the handle assembly without the user having to push down on the back of the teeter valve 204. This allows the container 100 to be carried in a backpack while the handle assembly 1114 is locked or secured on a strap of the backpack near the user's hand or mouth. This way the user can obtain fluid easily while hiking or other activity without having to reach container 100. The fluid is released simply by handling only the handle assembly 1114.

Figure 15A:
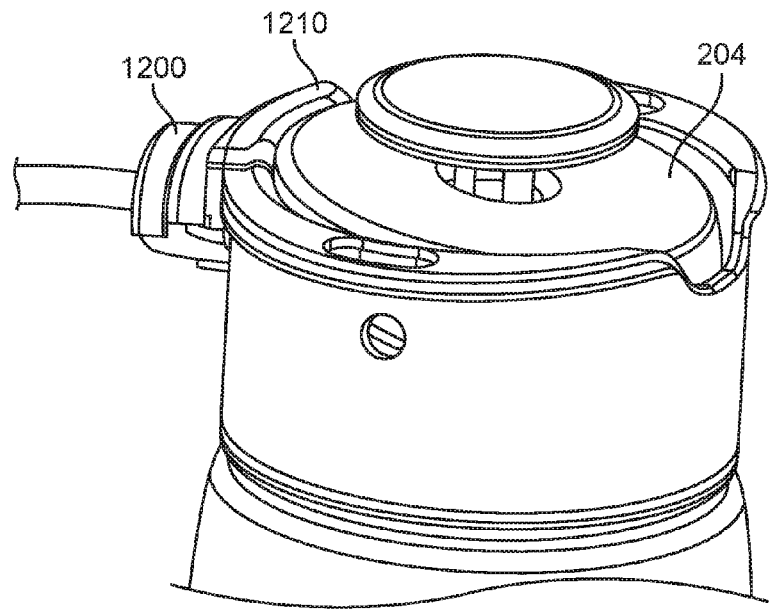
FIG. 15a is a perspective view of the trigger lock shown in FIG. 15a as used on a the cap of the pressurized container shown in FIG. 1.
Figure 15B:
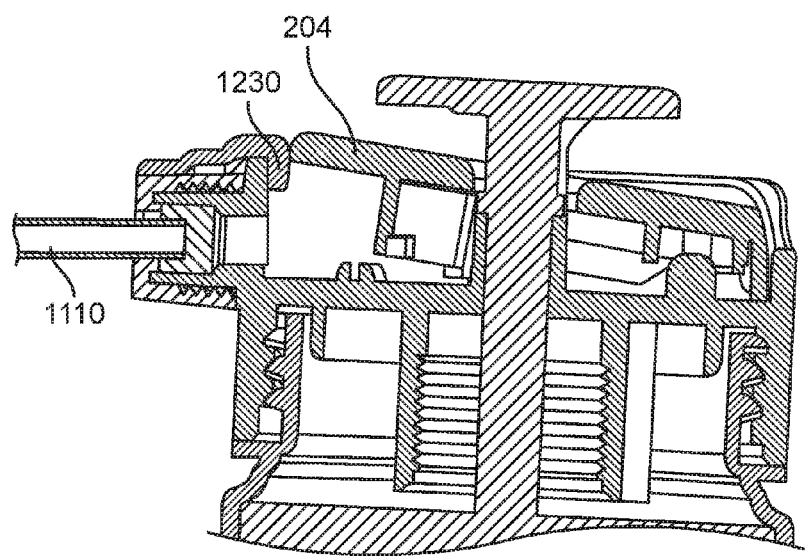

Trigger lock 1200 has a bottle cap grip 1210, a nozzle hood 1220, and a trigger lip 1230. Nozzle hood 1220 is shaped to blanked nozzle 116 on cap 110 of container 100, and bottle cap grip 1210 fits atop the rim of cap 110. As shown in FIGS. 15*a* and 15*b*, trigger lip 1230 is wedged between the rim of cap 110 and teeter valve 204, thus tilting the front side of teeter valve 204 up and off flexible conduit 322. This allows for the flow of pressurized fluid through nozzle 116 and into flexible tube 1110 and handle assembly 1114.

While the invention is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

We claim:

1. A flexible dispensing apparatus for coupling to pressurized fluid containers, said flexible dispensing apparatus comprising: a flexible tube with a first end and a second end, said first end comprising a nozzle connector for connecting the flexible tube to a pressurized fluid container; and a handle assembly housing the second end of the flexible tube, the handle assembly comprising a first side connected to a second side, a slide trigger, a roller coupled to the bottom of the slide trigger with a dowel pin, a spray nozzle assembly, a magnet reservoir, and a magnet, wherein the first side of the handle assembly has an integrated inclined ramp that runs along a length of the first side and extends into the second side above and beyond a seam that is formed by the connection of the two sides, and wherein the flexible tube is housed within a channel in the handle assembly formed between the inclined ramp and the roller, such that when the roller is rolled toward the end of the ramp with the slide trigger it pinches the flexible tube near the top of the inclined ramp thereby prohibiting the flow of fluid to the spray nozzle assembly; wherein the spray nozzle assembly comprises a first threaded nozzle formed integrally with a distal end of the first side of the handle assembly, a barbed fitting with a proximal end that is nested within the first threaded nozzle, an outlet nozzle with three or more shower holes, the outlet nozzle being coupled to a distal end of the barbed fitting, and an outlet cap having a single fluid outlet hole, wherein the outlet cap is fitted over the outlet nozzle, the outlet cap having a threaded portion that mates with the first threaded nozzle by screwing the outlet cap onto the first threaded nozzle, wherein the spray nozzle assembly is capable of releasing pressurized fluid as a stream or as a mist by adjusting how tightly the outlet cap is screwed onto the first threaded nozzle, or as a shower spray by completely removing the outlet cap.

2. The flexible dispensing apparatus of claim 1, wherein the first threaded nozzle comprises a pair of opposing anti-rotation notches that mate with a pair of corresponding anti-rotation protuberances on the outlet nozzle, such that when the outlet cap is fitted over the outlet nozzle and screwed onto the first threaded nozzle, the outlet nozzle is prohibited from rotating with the outlet cap.

3. A fluid containment and delivery system comprising: a pressurized fluid container having a cap comprising a threaded cap nozzle; and a flexible dispensing apparatus, said flexible dispensing apparatus comprising: a flexible tube with a first end and a second end, said first end comprising a threaded nozzle connector for connecting the flexible tube to the threaded cap nozzle of the pressurized fluid container; and a handle assembly housing the second end of the flexible tube, the handle assembly comprising a first side connected to a second side, a slide trigger, a roller coupled to the bottom of the slide trigger with a dowel pin, a spray nozzle assembly, a magnet reservoir, and a magnet, wherein the first side of the handle assembly has an integrated inclined ramp that runs along a length of the first side and extends into the second side above and beyond a seam that is formed by the connection of the two sides, and wherein the flexible tube is housed within a channel in the handle assembly formed between the inclined ramp and the roller, such that when the roller is rolled toward the end of the ramp with the slide trigger it pinches the flexible tube near the top of the inclined ramp thereby prohibiting the flow of fluid to the spray nozzle assembly; wherein the spray nozzle assembly comprises a first threaded nozzle formed integrally with a distal end of the first side of the handle assembly, a barbed fitting with a proximal end that is nested within the first threaded nozzle, an outlet nozzle with three or more shower holes, the outlet nozzle being coupled to a distal end of the barbed fitting, and an outlet cap having a single fluid outlet hole, wherein the outlet cap is fitted over the outlet nozzle, the outlet cap having a threaded portion that mates with the first threaded nozzle by screwing the outlet cap onto the first threaded nozzle, wherein the s pray nozzle assembly is capable of releasing pressurized fluid as a stream or as a mist by adjusting how tightly the outlet cap is screwed onto the first threaded nozzle, or as a shower spray by completely removing the outlet cap.

4. The flexible dispensing apparatus of claim 3, wherein the first threaded nozzle comprises a pair of opposing anti-rotation notches that mate with a pair of corresponding anti-rotation protuberances on the outlet nozzle, such that when the outlet cap is fitted over the outlet nozzle and screwed onto the first threaded nozzle, the outlet nozzle is prohibited from rotating with the outlet cap.

\* \* \* \* \*